Figure 5:
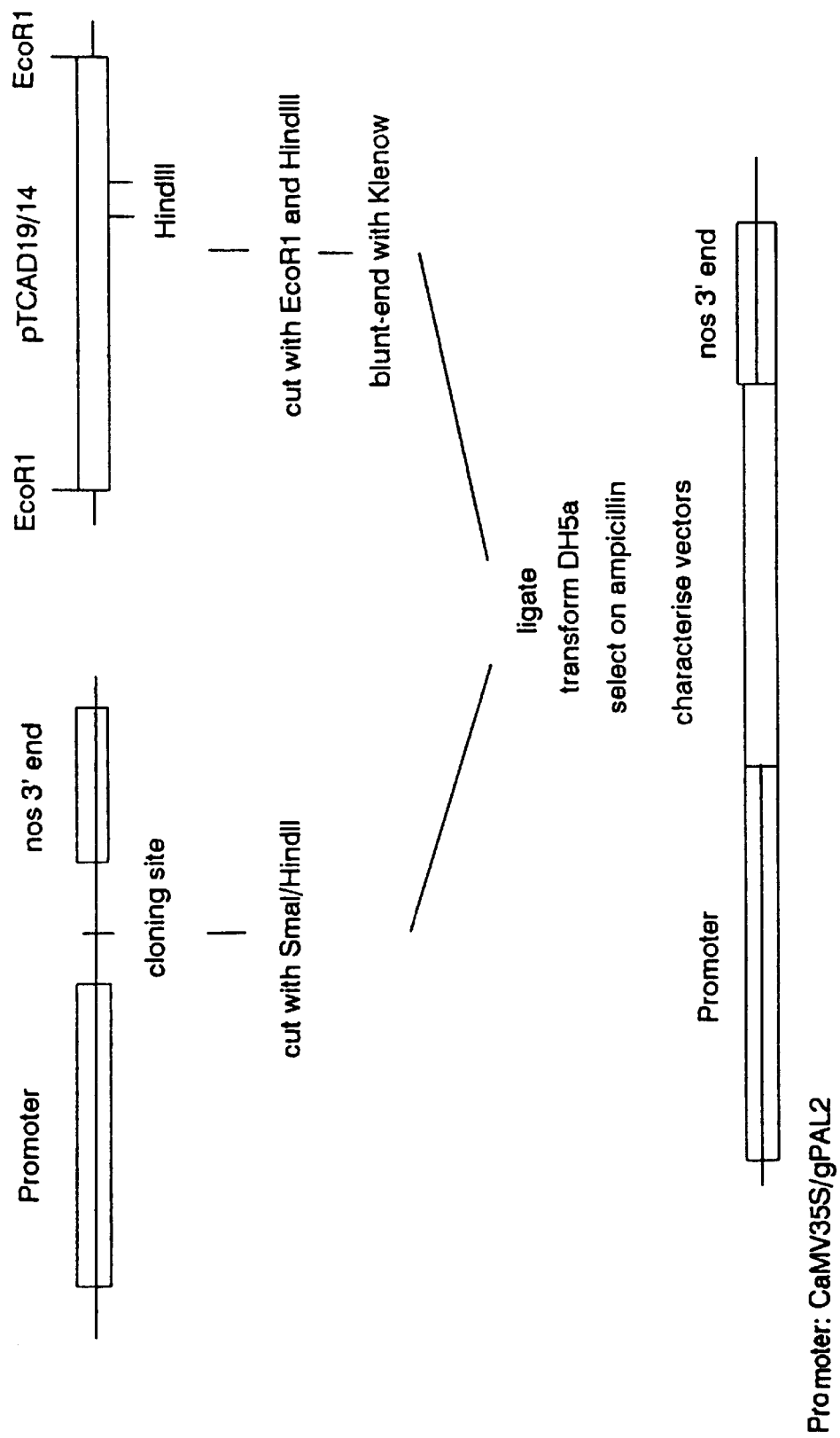

US006066780A

United States Patent [19]
Boudet et al.

[11] Patent Number: 6,066,780
[45] Date of Patent: *May 23, 2000

[54] MODIFICATION OF LIGNIN SYNTHESIS IN PLANTS

[75] Inventors: Alain Michel Boudet, Toulouse, France; Dirk Gustaaf Inze, Aalst, Belgium; Wolfgang Walter Schuch, Heathlake Park, United Kingdom

[73] Assignee: Zeneca Limited, London, United Kingdom

[*] Notice: This patent is subject to a terminal disclaimer.

[21] Appl. No.: 08/452,071

[22] Filed: May 26, 1995

Related U.S. Application Data

[63] Continuation of application No. 08/174,467, Dec. 28, 1993, Pat. No. 5,451,514, which is a continuation of application No. 07/874,166, Apr. 27, 1992, abandoned.

[30] Foreign Application Priority Data

Apr. 26, 1991 [GB] United Kingdom .................... 9109063

[51] Int. Cl.$^7$ .............................. A01H 5/00; C12N 15/82
[52] U.S. Cl. ......................... 800/278; 800/298; 536/23.6
[58] Field of Search .................................. 800/205, 298, 800/278; 536/23.1, 23.6, 24.5; 435/172.3, 240.4, 419, 468

[56] References Cited

U.S. PATENT DOCUMENTS

| | | | |
|---|---|---|---|
| 4,394,443 | 7/1983 | Weissman et al. | ......................... 435/6 |
| 5,034,423 | 7/1991 | Jorgensen et al. | ................... 435/172.3 |

FOREIGN PATENT DOCUMENTS

| | | |
|---|---|---|
| 2005597 | 12/1989 | Canada . |
| 0240208 | 10/1987 | European Pat. Off. . |
| WO9012084 | 12/1990 | WIPO . |
| WO9305160 | 3/1993 | WIPO . |
| WO9324638 | 12/1993 | WIPO . |

OTHER PUBLICATIONS

Napoli et al (1990) The Plant Cell 2: 279–289.
Grand et al (1985) Planta 163: 232–237.
Walter et al (1988) Proce. Natl Acad Sc USA 85:5546–5550.
Delaney et al (1988) Proc. Natl Acad Sci USA 85:4300–4304.
Sarni et al (1984) Eur. J. Biochem 139:259–265.
Bevan et al (1989) EMBO J. 8 (7):1899–1906.
Rhodes et al (1988) Science 240:204–207.
Van der Krol (1988) Nature 333:866–869.
Lewin, R. (1987) Science 237:1570.
Cannon et al, "Organ–specific modulation of gene expression in transgenic plants using antisense RNA", Plant Molecular Biology 1990, 15:39–47.
Crooke, Stanley T., M.D. (ed.) Antisense Research and Applications, CRC, pp. 125–148.
Bird et al, "Manipulation of Plant Gene Expression by Antisense RNA", Biotechnology and Genetic Engineering Reviews, vol. 9, Dec. 1991, pp. 207–227.

O'Malley et al, "Purification and Characterization of Cinnamyl Alcohol Dehydrogenase from Developing Xylem of Loblolly Pine, and its Role in Strategies to Modify the Lignin Content of Wood", J. Cellular Biochemistry, Abstracts 19th Annual Meetings, Mar. 31–Apr. 22, 1990, No. R 532, p. 355.
Schuch et al, "Transgenic plants having reduced lignin or lignin of altered quality", Chemical Abstracts, vol. 114, 1991, No. 114:222827m.
Loopstra et al, "Isolation of Genes with Enhanced Expression in Xylem Tissue of Loblolly Pine," J. Cellular Biochemistry, Abstracts 19th Annual Meetings, Mar. 31–Apr. 22, 1990, No. R 525, p. 353.
Grima–Pettenati et al, "Inhibition of Cinnamyl Alcohol Dehydrogenase Synthesis in Stably Transformed Tobacco Plants Expressing Antisense RNA", J. Cellular Biochemistry, Abstracts 19th Annual Meetings, Mar. 31–Apr. 22, 1990, No. R 511, p. 348.
O'Malley et al, "Purification, Characterization, Cloning of Cinnamyl Alcohol Dehydrogenase in Loblolly Pine (*Pincus Taeda L.*)", Plant Physiol. (1992) 98, 1364–1371.
Sarni et al, "Purification and properties of cinnamoyl–cocaxyme A reductase (EC 1.2.1.44) and clamamyl alcohol alcohol dehydrogenase (EC 1.1.1.1) from poplar stems (*Populus euramericana*)," Biological Abstracts, vol. 78, (1984) No. 14461, p. 1647.
Elkind et al, "Abnormal plant development and down–regulation of phenylpropanoid biosynthesis in transgenic tobacco containing a heterologous phenylalanine ammonia–lyase gene," Proc. Natl. Acad. Sci. U.S.A. vol. 878, Nov. 1990, pp. 9057–9061.
Rothstein et al, "Inhibition of Nopaline Synthase and Peroxidase Expression in Tobacco Expressing Antisense RNA" Plant Gene Transfer, 1990, pp. 135–141.
Halpin et al, "Purification and Characterization of Cinnamyl Alcohol Dehydrogenase from Tobacco Stems," Plant Physiol. 98 (1992) p. 12–16.
Halpin et al, "Manipulation of lignin quality by downregulation of cinnamyl alcohol dehydrogenase", The Plant Journal 6(3) 1994 p. 000–000.
Jacobs et al (1985) Nature 313:806–809.
Leonard et al (1984) Nature 311:626–631.
Matsudaira, P. (1987) J. Biol. Chem 262 (21):10035–10038.
Matsudaira, P. (1990), Methods in Enzymology 182:602–613.
Kim et al (1994) Plant Mol. Biol 24: 105–117.

*Primary Examiner*—Elizabeth F. McElwain
*Attorney, Agent, or Firm*—IP Group of Pillsbury Madison & Sutro

[57] ABSTRACT

The synthesis of lignin by plants is controlled by transformation of the plant genome with a recombinant gene construct which contains the gene specifying an enzyme critical to the synthesis of a lignin precursor, which gene may be in antisense orientation so that it is transcribed to mRNA having a sequence complementary to the equivalent mRNA transcribed from the endogenous gene thus leading to suppression of lignin synthesis. If the recombinant gene has the lignin enzyme gene in normal, or "sense" orientation, increased production of the enzyme may occur when the insert is the full length DNA but suppression may occur it only a partial sequence is employed.

4 Claims, 14 Drawing Sheets

FIG. 1

| Peak 1 (44kDa) | Peak 2 (42 kDa) |
|---|---|

N-TERMINAL SEQUENCE

| K/SXLXV | K/SLXV |
|---|---|

INTERNAL SEQUENCE

| | | |
|---|---|---|
| 1 | TTIGXAAIVK | TAIGQAAIV |
| 2 | FPSDVLRPYTYTLD | PSGLLSPYTYTLV |
| 3 | FVVDVIGK | FVVDVAGD |
| 4 | MDYINGAMER | DYINTAMG/E |
| 5 | RTLGMSN | NDLGMSNYP |
| 6 | AMGXXVXVI | |
| 7 | AV/ITPYFD/Y | |
| 8 | SGILGL | |

FIG. 2

ATG GAT/C TAT/C ATT/C/A AAT/C GGI GCI ATG GA

FIG. 3A

SEQ ID NO:17
SEQUENCE TYPE:Nucleotide
SEQUENCE LENGTH:1419 base pairs
STRANDEDNESS:single
TOPOLOGY:linear
MOLECULAR TYPE:cDNA ORIGINAL SOURCE ORGANISM:tobacco var. Samsun
IMMEDIATE EXPERIMENTAL:tobacco stem cDNA library

FEATURES from 93 - 1165 open reading frame
PROPERTIES: cDNA of cinnamyl alcohol dehydrogenase-pTCAD19

FIG. 3B

```
ATTTCTTTCT CTTTCCCTTG AACTGTGTTT TCATTTTTTC TGCTCTGAAA CAATAGTGTT    60
TTCCTTGTAG ATTTTAAGTT AAAAGAAAAC CATGGGTAGC TTGGATGTTG AAAAATCAGC   120
TATTGGTTGG GCTGCTAGAG ACCCCTTCTGG TCTACTTTCA CCTTATACCT ATACTCTCAG  180
AAACACAGGA CCTGAAGATG TGCAAGTCAA AGTTTTGTAT TGTGGACTTT GCCACAGTGA   240
TCTTCACCAA GTTAAAAATG ATCTTGGCAT GTCCAACTAC CCTCTGGTTC CTGGACATGA   300
AGTGGTGGGA AAAGTAGTGG AGGTAGGAGC AGATGTGTCA AAATTCAAAG TGGGGACAC    360
AGTTGGAGTT GGATTACTCG TTGGAAGTTG TAGGAACTGT GGCCCTTGCA AGAGAGAAAT   420
AGAGCAATAT TGCAACAAGA AGATTGGGAA TTGCAATGAT GTCTACACTG ATGGCAAACC   480
CACCCAAGGT GGTTTTGCTA ATTCTATGGT TGTTGATCAA AACTTTGTGG TGAAAATTCC   540
AGAGGGTATG GCACCAGAAC AAGCAGCACC TCTATTATGT GCTGGCATAA CAGTATACAG   600
TCCATTCAAC CATTTTGGTT TTAATCAGAG TGGATTAGA GGAGAATTT TGGGATTAGG    660
AGAGTTGGA CATATGGGAG TGAAAAATAGC AAAGGCAATG GGACATCATG TTACTGTCAT   720
TAGTTCTTCA AATAAGAAGA GACAAGAGGC ATTGGAACAT CTTGGTGCAG ATGATTATCT   780
TGTTAGTTCA GACACTGATA AAATGCAAGA AGCTGCTGAT TCACTTGACT ATATTATTGA   840
TACTGTCCCT GTTGGCCATC CTCTTGAACT TTATCTTTCT TTGCTTAAAA TTGATGGCAA   900
ACTTATCTTG ATCGGAGTTA TCAACACCCCC CTTGCAATTT ATCTCTCCCA TGGTTATGCT   960
CGGGAGAAAG AGCATCACTG GAAGCTTTAT TGGTAGCATG AAGGAAACAG AGGAAATGCT  1020
AGACTTCTGC AAAGAGAAAG GTGTGACTTC ACAGATTGAG ATAGTGAAAA TGGATTATAT  1080
CAACACTGCA ATGGAGAGGT TGGAGAAAAA TGATGTGAGC TACAGATTTG TTGTTGATGT  1140
TGCTGGAAGC ATGGAGCTTGACC AGTAATTGCA CAAGAAAAAC AACATGGAAT GGTTCACTAT  1200
TATACAACAA GGCTATGAGA AAAATAGTAC TCCTCAACTT TGATGTCATC TTTGTTACCT  1260
TTGTTTTATT TTCCACCTGT ATTATCATAT TGGTGGTCG AGAGTGACGT TTATGTATAT  1320
TTTCTTTCTT CAAAACAATC TTAAATGAAT TTGGATGTTG GTGACGATTT TGAAATATAC  1380
CAACCATGCA AACTTACTTT GGTAGAAAAA AAAAAAAA                          1419
```

FIG. 4A

SEQ ID NO: 18
SEQUENCE TYPE: Nucleotide
SEQUENCE LENGTH: 1393
STRANDEDNESS: single
TOPOLOGY: linear
MOLECULAR TYPE: cDNA ORIGINAL SOURCE ORGANISM: tobacco var. Samsum
IMMEDIATE EXPERIMENTAL: tobacco stem cDNA library

FEATURES:

from 84 - 1155 open reading frame

PROPERTIES: cDNA of cinnamyl alcohol dehydrogenase - pTCAD14

FIG. 4B

```
TCTTTCCCTT GAACTGTGTT TTCGTTTTTT CTGCTCTAAA ACAATCGTGT GTTCCTTGTA   60
GATTTAAGT  TTAAAGAACA TCATGGGTGG CTTGGAAGTT GAGAAAACAA CTATTGGTTG  120
GGCTGCTAGA GACCCTTCTG GTGTACTTTC ACCTTATACC TATACTCTCA GAAACACAGG  180
ACCTGAAGAT GTGGAAGTCA AAGTTTTGTA TTGTGGGCTC TGTCACACTG ATCTTCACCA  240
AGTTAAAAAT GATCTTGGCA TGTCCAACTA CCCTCTGGTT CCTGGACATG AAGTGGTGGG  300
AGAAGTGGTG GAGGTAGGAC CAGATGTGTC AAAATTCAAA GTTGGGGACA CAGTGGAGT   360
TGGATTACTC GTTGGAAGTT GCAGGAAACT TGGCCCTTGC AAGAGAGATA TAGAGCAATA  420
TTGCAACAAG AAGATTTGGA ACTGCAATGA TGTCTACACT GATGCAAAAC CCACCCAAGG  480
TGGTTTTGCT AAATCCATGG TTGTTGATCA AAGTTTGTG GTGAAAATTC CAGAGGGTAT  540
GGCACCAGAA CAAGCAGCAC CTCTATTATG TGCTGGTATA ACAGTATACA GTCCATTGAA  600
CCATTTGGT  TTCAAACAGA GTGGAGGAAT AGGAGGAATT TTGGGATTAG GAGGAGTGGG  660
ACACATGGGA GTGAAATTGG CAAAGGCAAT GGGACATCAT GTTACTGTCA TTAGTTCTTC  720
AATAAGAAG  AGACAAGAGG CATTGGAACA TCTTGGTGCA GATGATTATC TTGTCAGTTC  780
AGACACTGAT AAAATGCAAG AGGCTTCTGA TTCACTTGAC TATATTATTG ATACTGTCCC  840
TGTTGGCCAT CCTCTCTTTG CTTATCTTTC TTTGCTTAAA ATTGATGGCA AACTTATCTT  900
GATGGGAGTT ATCAACACCC CCTTGCAATT TATCTCCCCC ATGGTTATGC TCGGGAGAAA  960
GAGCATCACA GGAAGCTTTA TTGGGTAGCAT GAAGGAAACA GAGGAAATGC TAGATTTCTG 1020
CAAAGAGAAA GGTGTGACTT CACAGATTGA AATGATTATA TCAACACTGC TTATTGGAAG 1080
AATGGAGAGG TTGGAGAAAA ATGATGTGAG GTACAGATTT GTGGTTGATG TTATTGGAAG 1140
CAAGCTTGAC CAGTAATTAT ATTACACAAG AAAAACAACA TGGAATGGTT CACTATTATA 1200
CAAGGCTGTG AGAATACTAA ACTTTGATGT CGTCTTTTGT ATCCTTTTGT TTTATTGCC  1260
ACCTGTATT  TCTTATTTGG TGATCGAGAG TGACGTTTAT GTATTATTTT CTTCTTTCAA 1320
AACAATTTAA TGTATGAATT TGGATGTTGG TGAAAAAAAA AAAAAAAA              1380
AAAAAAAAA  AAA                                                    1440
```

FIG. 7A

SEQ ID NO: 19
SEQUENCE TYPE: Nucleotide
SEQUENCE LENGTH: 1285
STRANDEDNESS: single
TOPOLOGY: linear
MOLECULAR TYPE: cDNA ORIGINAL SOURCE ORGANISM: poplar
IMMEDIATE EXPERIMENTAL: poplar xylem cDNA library

FEATURES:

from 28 - 1099 open reading frame

PROPERTIES: cDNA of cinnamyl alcohol dehydrogenase - pPOPCAD1

FIG. 7B

```
CTCTCTTAGC CTCATTGTTT CAAGAAAATG GGTAGCCTTG AAACAGAGAG AAAAATTGTA   60
GGATGGGCAG CAACAGACTC AACTGGGCAT CTCGCTCCTT ACACCTATAG TCTCAGAGAT  120
ACGGGGCCAG AAGATGTTTT TATCAAGGTT ATCAGTTGTG GAGTTTGCCA TACCGATATC  180
CACCAAATCA AAAATGATCT TGGCATGTCA CACTATCCTA TGTCCCCTGG CCATGAAGTG  240
GTTGGTGAGG TTGTTGAGGT GGGATCAGAT GTGACAAGGT TCAAAGTTGG AGATGTTGTC  300
GGTGTTGGAG TCATCGTTGG AAGCTGCAAG AATTGTCATC CATGCAAATC AGAGATTGAG  360
CAATACTGCA ACAAGAAAAT CTGGTCTTAC AATGATGTCT ACACTGATGG CAAACCCACC  420
CAAGGAGGCT TTGCTGAATC CATGGTTGTG CATCAAAAGT TTGTGGTGAG AATTCCTGAT  480
GGGATGTCAC CAGAACAAGC AGCGCCGCTA TTGTGCGCTG GATTGACAGT TTACAGCCCA  540
CTTAAACACT TTGGACTGAA ACAGAGTGGG CTAAGAGGAG GGATTTTAGG ACTTGGAGGA  600
GTAGGGCACA TGGGGGTGAA GCAATGGGAC ACCATGTAAC TGTGATTAGT  660
TCTTCTGACA AGAAGCGGGA GGAGGCTATG GAACATCTTG GTGCTGATGA ATACTTGGTC  720
AGCTCGGATG GCAAAAAGCT GCTGATCAAC TTGATTATAT CATCGATACT  780
GTGCCTGTGG TTCACCCTCT GGAGCCTTAC CTTTCTCTGT TGAAACTTGA TGGCAAGCTG  840
ATCTTGATGG GTGTTATTAA TGCCCCATTG CAGTTTGTTA CGCCTATGGT TATGCTTGGG  900
AGAAAGTCTA TCACCGGGAG CTTCATAGGG AGCATGAAGG AGACAGAGGA GATGCTTGAG  960
TTCTGCAAGG AAAAGGGAGT GGCCTCCATG ATTGAAGTGA TCAAAATGGA TTATATCAACA 1020
ACVGCATTCG AGAGGCTTGA GAAAAATGAT GTGAGATATA GATTCGTTGT CGATGTTGCT 1080
GGTAGCAAGC TTATTCACTG AACAACAATA CTCTTCATAT TCGAAAAAAA AACGATATAC 1140
ATTGATACCT GTTTCAGACG TGACTTTATT TCCGAGTGAT GTGTTTGTG GATCAAATGT 1200
GACAGTGTGT CTTTGCTTTT AAATAAAGA AAAGGTTGAA TTGTTTTTTT NAAAAAAA AGT 1260
AAAAAAAAAA AAAAAAAAA AAAAA                                       1320
```

FIG. 8A

SEQ ID NO: 20
SEQUENCE TYPE: Nucleotide
SEQUENCE LENGTH: 1385
STRANDEDNESS: single
TOPOLOGY: linear
MOLECULAR TYPE: cDNA ORIGINAL SOURCE ORGANISM: eucalyptus gunnii (clone 832, AFOCEL)
IMMEDIATE EXPERIMENTAL: eucalyptus suspension culture cDNA library

FEATURES:

from 105 - 1173 open reading frame

PROPERTIES: cDNA of cinnamyl alcohol dehydrogenase - pEUCAD1

FIG. 8B

```
CTGCTCCCTAC CCGCAACTTC CCATCTACAT AAGCAGCAAG TTTACGGCTC TGTCGAATCT   60
CTCTCCGAGC ACCACTTTGA AAGAAGCTTG GATCTTTGAG CAAAAATGGG CAGTCTTGAG  120
AAGGAGAGGA CCACCACGGG TTGGGCTGCA AGGGACCCGT CTGGCGTTCT CTCTCCTTAC  180
ACTTATAGCC TCAGAAACAC GGGACCAGAA GATCTTTACA TCAAGGTGTT GAGCTGCGGA  240
GTTGCCACA GTGACATTCA CCAGATCAAG AATGATCTTG GCATGTCCCA CTACCCTATG  300
GTTCCTGGGC ATGAAGTGGT GGGCGAGGTT CTGGAGGTGG GATCAGAGGT GACAAAGTAC  360
AGAGTTGGTG ACCGAGTGGG AACCGGTATA GTGGTTGGGT GCTGCAGAAG CTGTAGCCCT  420
TGCAATTCGG ACCAGGAGCA ATATTGCAAC AAGAAGATTT GGAATTACAA TGACGTGTAC  480
ACCGATGGCA AGCCCACTCA AGTGGGTTT GCTGGTGAGA TAGTGGTTGG CGAAAGGTTT  540
GTGGTGAAAA TCCCAGATGG GTTAGAGTCG GAACAGGCAG CGCCGCTGAT GTGCGCTGGT  600
GTGACCCGTGT ACAGCCCCTCT GGTGCGCTTT GGGCTCAAGC AAAGCGGGTT GAGAGGAGGG  660
ATATTGGGGC TTGGAGGGGT TGGCCACATG GGGTGAAGA TAGCCAAGGC CATGGGACAC  720
CACGATGACTG TGATAAGCTC TTCTGATGAA AAGAGAACGG AGCCATTGGA GCACCTGGGT  780
GCCGATGCTT ACCTAGTGAG CTCCGATGAA AATGGAATGA AAGGAGCCAC TGATTCTCTC  840
GACTACATTT TGACACTAT CCCTGTGGTT CACCCCTCTG AACCTTACCT GGCCTTGTTG  900
AAGCTCGATG GAAAGCTGAT CTTGACTGGT GTCATCAATG CTCCTCTTCA ATTTATCTCT  960
CCCATGGTTA TGCTTGGGAG CAAGTCAATC ACTGGGAGTT TCATAGGGAG CATGAAGGAA 1020
ACAGAGGAGA TGCTTGAGTT CTGCAAAGAA AAGGGATTGA CTTCCCAGAT CGAAGTGATC 1080
AAGATGGATT ATGTCAACAC CGCCCCTAGA AGGCTCGAGA AGAATGATGT CAGGTACAGG 1140
TTCGTCGTGG ACGTCGTGGG AAGCAAGCTT GATTAGTTTC GGCTTTCCCC ATAAGTAAAC 1200
AAGAAATCGA CTTGCTTGTC TCTCAATTCG AGTTCCTCAT GCCCTCTGTT GTATCATTGT 1260
TTGTTATACC GAGAGTGCTA TCTTCGTATT TCTTCGTATT GAAACCATAG ACCTTCTCGA 1320
TTGTGTATTC AATGATGAAG GTGTTAATGA TTTTATCACT TAAAAAAAAA AAAAAA      1380
```

FIG. 9

PCR primers used to isolate a maize CAD gene fragment

```
ZCAD3    CAT  GAA  GTG  GTI  GGI  GAG  GTI  GTI  GAG  G
          C    G    C              A

ZCAD2    GGT  TTI  CCG  TCI  GTG  TAC  ACA  TCA  TTG
          C         A              G    G
                                    G
```

FIG. 10

```
SEQ ID NO: 23
SEQUENCE TYPE: Nucleotide
SEQUENCE LENGTH: 180
STRANDEDNESS: single
TOPOLOGY: linear
MOLECULAR TYPE: genomic fragment ORIGINAL SOURCE ORGANISM: maize
IMMEDIATE EXPERIMENTAL: pcr product from genomic DNA

FEATURES:

from 1-180 open reading frame

PROPERTIES: genomic fragment of cinnamyl alcohol dehydrogenase -
pZCAD1

GGTGGTGGGG GAGGTGGTGG AGGTCGGGCC CGAGGTGGCC AAGTACGGCT TCGGCGACGT  60
GGTAGGCGTC GGGGTGATCG TTGGGTCGTG CCGCGAGTGC AGCCCCTGCA AGCCAACGT  120
TGAGCAGTAC TGCAACAAGA AGATCTGGTC ATACAACGAC GTCTACACCG ACGGCAAACC  180
```

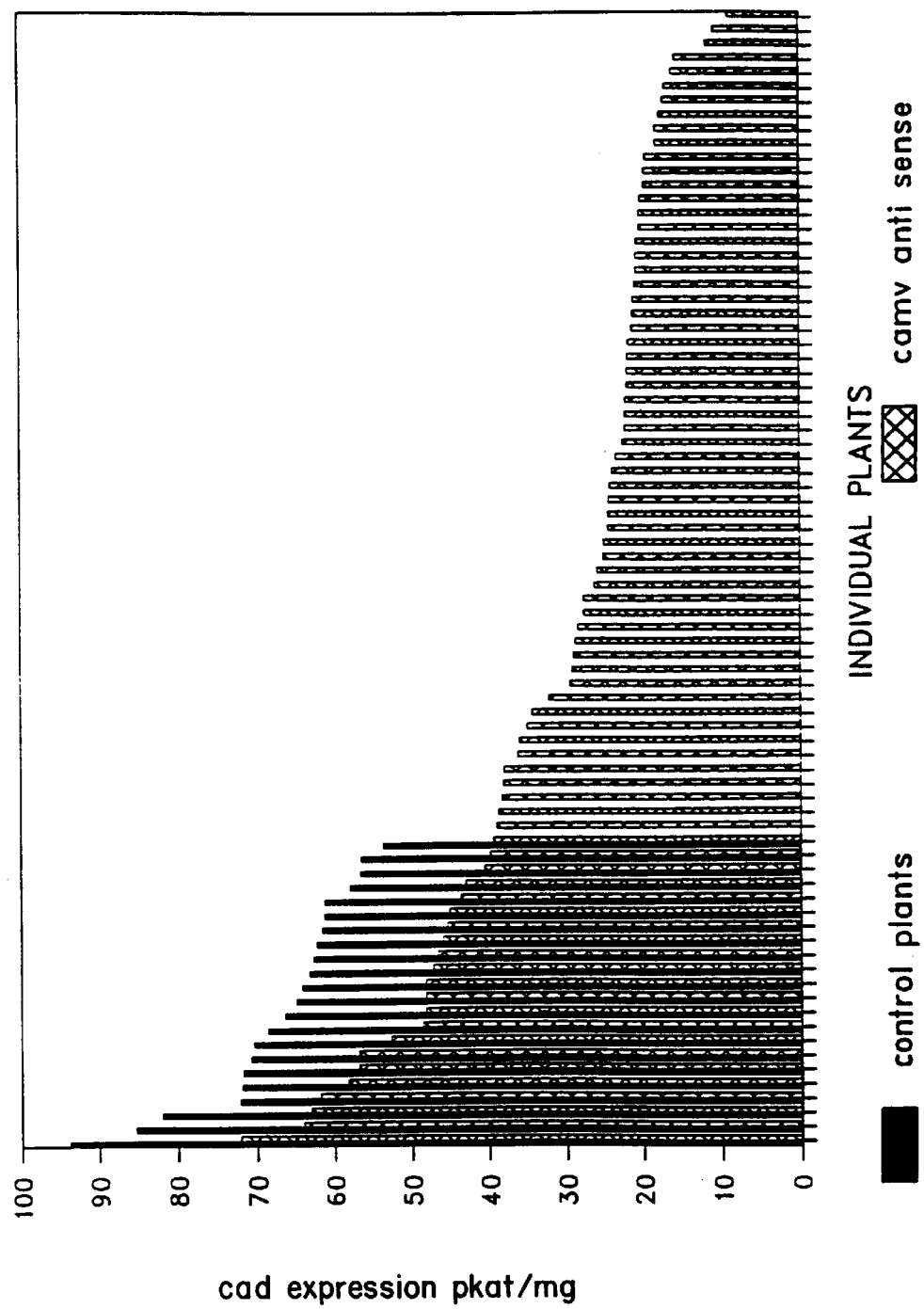

MODIFICATION OF LIGNIN SYNTHESIS IN PLANTS

This is a continuation of application Ser. No. 08/174,467, filed Dec. 28, 1993, now U.S. Pat. No. 5,451,514 which is a continuation of application Ser. No. 07/874,166, filed on Apr. 27, 1992, now abandoned.

This invention relates to the improvement of plants by the modification of lignin biosynthesis, particularly, but not exclusively, the improvement of digestibility of fodder crops.

Grassland farmers, and farmers of other fodder crops, face a difficult decision each year about when to cut their crops for conservation. All grass varieties of agricultural importance suffer from the disadvantage that during the normal increase in dry matter yield with growth, the digestibility decreases. The farmer, therefore, has to compromise between a lower yield of highly digestible material and a higher yield of less digestible material. Another limitation is that harvesting at optimum maturity may be prevented by unfavourable weather. If the decline in digestibility could be controlled or delayed, higher yields of highly digestible material could be obtained and the prevailing weather conditions would not play such a major role in determining the quality of the harvested crop.

Digestibility of fodder crops is determined, among other factors, by the amount of lignification which has taken place during growth of the plants and the degree of secondary modification of lignin deposited. Beside cellulose and other polysaccharides, lignins are an essential component of the call wall in tissues like the sclerenchyma and the xylem of vascular plants. They play an Important role in the conducting function of the xylem by reducing the permeability of the cell wall to water. They are also responsible for the rigidity of the cell wall, and, in woody tissues, they act as a bonding agent between cells, imparting to the plant a resistance towards impact, compression and bonding. Finally, they are involved in mechanisms of resistance to pathogens by impeding the penetration or the propagation of the pathogenic agent.

Lignins are not only important in the productivity and performance of field crops but are also of great importance in trees for paper making. Considerable energy and chemical input is required to loosen, dissolve and remove lignin from the cellulose fibre which is required for paper making.

In addition to these instances in which lignins present a constraint on the use of crop plants, lignins are also used as feedstocks for the preparation of speciality chemicals such as phenolics which can be used as precursors in chemical synthesis. Thus lignins and their biological and chemical modification are important.

It is one of the objects of the present invention to provide a biotechnological procedure for the modification of both lignin content and lignin composition in plants.

Lignins are the product of a dehydrogenative polymerization of three primary precursors: the trans-coniferyl, trans-sinapyl and trans-p-coumaryl alcohols. The monomers can occur in lignins in different proportions and with different types of linkages both with each other and with the surrounding cell wall polysaccharides, thus producing a wide variety of polymers. These polymers, or "lignin cores" are always associated covalently with hemicelluloses. Most lignins also contain varying amounts of aromatic carboxylic acids in ester-like combinations. Such differences in the structure of lignins are usually found in plant species. However, differences in the composition of lignins, and even in the binding to the primary and secondary cell walls, can also occur in the sate plant, between different tissues of different ages. The biosynthesis of lignin monomers is a part of the phenylpropanoid biosynthesis pathway, which in also responsible for the production of a wide range of compounds including flavonoid pigments, isoflavonoids, coumarin phytoalexins and cell division promoting dehydrodiconiferyl glucosides.

Phenylalanine is deaminated to produce cinnamic acid. This acid is then hydroxylated and methylated, producing different acids substituted on the aromatic ring. Coenzyme A thioesters of (p)-coumaric, ferulic and sinapic acids are then produced by the action of hydroxycinnamate: CoA ligase. These compounds are subsequently reduced by cinnaxyl-CoA reductase (CCR) to cinnamaldehydes, which are finally converted to cinnamyl alcohols by the cinnamyl alcohol dehydrogenase (CAD). Only the last two reactions are specific for the biosynthesis of lignin. The cinnamyl alcohols are then believed to be transported to the cell wall where they are polymerized by peroxidase in the presence of hydrogen peroxide.

When the surface growth of the cell ceases, it is followed by a phase of wall thickening (secondary wall formation). Lignification takes place predominantly during this phase. It starts in the cell corners and extends along the middle lamella, through the primary wall and, finally, to the secondary wall. External factors can induce qualititave and quantitative modifications in lignification. The synthesis of new types of lignins, sometimes in tissues which are not normally lignified, may be induced by infection with pathogenic microorganisms. Lignification is stimulated by light, as well as by low calcium levels, by boron, by mechanical stress and by infection.

Cinnamyl alcohol dehydrogenase: (CAD, E.C. 1.1.1.195) catalyses the conversion of cinnamaldehydes to cinnamyl alcohols. CAD has been characterised for several different species; *Forsythia suspensa,* soybean (*Glycine max*), spruce (*Picea abies*), poplar (*Populus euramericana*) and eucalyptus.

In most instances, only one form of CAD, has been detected for each species except for soybean which has two isoenzymes, one of 43,000 daltons and one of 69,000 daltons. The first soybean isoenzyme is specific for coniferyl alcohol while the 69,000 daltons soybean-isoenzyme and all other CAD can catalyse the formation of all the cinnamyl alcohols (i.e. coniferyl, sinapyl and coumaryl alcohols). However, the Km of CAD for the different cinnamyl alcohols varies between enzymes from different species. This variation may explain the different compositions of lignin core in different species. Indeed, lignin monomers cannot be synthesized in plants by any biochemical pathway not involving CAD and CCR. Thus CAD, as well as CCR, may be key enzymes in the regulation of lignification. The utilisation of inhibitors specific for these enzymes indicates that they may regulate the quantity of lignin rather than its composition. However, the Km values of soybean CAD isoenzymes for the different cinnamyl alcohols suggest that CAD isoenzymes may control the composition of lignin in some species. The presence of Zn2+ is required for the activity of CAD, as for other alcohol dehydrogenases. The reduction of cinnamaldehydes cannot be catalysed by CAD in the presence of NAD instead of NADP. The common sub-unit structure of CAD seems to be a dimer of approximately 80,000 daltons (each monomer having a molecular weight of approximately 40,000). However, it has been reported that the bean enzyme is a monomer with a molecular weight of 65,000, based on analysis of cDNA clones. Treatment of bean cell suspension cultures with a highmolecular-mass elicitor preparation heat-released from mycelial cell wall of the bean pathogen *Collectotrichum lindemuthianum* increases the extractable activity of CAD. The increased CAD activity might be regarded as a reaction of defense against pathogenic microorganisms, since an increase in the activity of this enzyme may be related to the deposition of lignin in the cell wall of infected cells, or to the synthesis of extracellular lignin-like material and other phenolic compounds involved in defense responses.

Walter et al. (1988) have constructed a lamda gt11 cDNA library from elicitor-treated been cells. This library was screened with antibodies raised against poplar CAD enzyme to identify the CAD Aoba clones. A 1.2 kb long cDNA alone was isolated and designated clone 4a. Subsequent experiments have however demonstrated that this clone does not encode CAD but malic enzyme (Walter et al., 1990).

Therefore, although it was known that CAD may be a useful target for the modification of crop plants, this was in fact not-practically possible using the information available. The work leading to the present invention provides a new method for the isolation of CAD enzyme to homogeneity, and CAD cDNA clones from various species, which can now be used to modify lignification of crop plants.

Thus, plants with a reduced amount of lignin or modified lignin composition would be more efficiently used as a forage for cattle. The yield or milk and meat would be therefore increased. Furthermore, lignin may have a negative effect on plant growth. Thus, a reduction of the lignification in crops such as wheat, oilseed rape, sugar beet or maize might presumably increase the grain yield. Trees with reduced lignin contents or altered lignin structure will lead to a reduction in the cost of the paper as less lignin will have to be removed during the pulping process. On the other hand, novel papers may be produced due to the purity of cellulose fibre which could otherwise not be produced.

The principal applications of the present invention are improvement of the digestibility of forage crops, reduction of lignin in woody feedstocks for cellulose fibre extraction, improvement of the response of crop plants to pathogen attack, and, improvement of timber quality. Some of these applications may require that the total amount of lignin be reduced; others may require that the amount of lignin be increased. It may also be the case that alteration of the chemical composition of the lignin polymer will confer advantages in the selected application.

Industrial processes for the extraction of cellulosic fibres from woody feedstocks amount in essence to a chemical extraction procedure for removing lignin. Once lignin is removed from the feedstock the cellulosic fibres may be recovered and manufactured into paper or utilised in other ways, for example the cellulose may be further processed into cellulosic films or yarn for weaving or knitting into fabrics. Reduction of the lignin synthesised by the plants used as feedstock, trees usually, will have a direct effect of reducing the chemical and energy demands of such extractive processes and reduce the amount of effluent material which well-recognised as a major potential environmental pollutant which is both difficult and expensive to process. Alteration of the chemical composition of the lignin will potentially alter the solubility characteristics of the lignin in the chemical extractants used. Again this should lead directly to a reduced usage of chemicals and lower energy requirements. Finally alteration of the lignin quality of presently unsuitable species may provide alternative feedstocks for the papermaking industry and the cut timber industry.

Reduction of lignification can be achieved by the application of chemical inhibitors to plants. However, a more effective method controlling lignin deposition and structure is the inhibition of expression of the CAD gene using antisense RNA. Antisense RNA technology is an appropriate molecular biology approach to the inhibition of lignification. An antisense RNA is an RNA produced by the transcription of the non-coding DNA strand (nonsense). Thus, antisense RNA has the same sequence as the coding DNA strand and is complementary to the mRNA product of a specific gene.

As is well known, a cell manufactures protein by transcribing the DNA of the gene for that protein to produce RNA, which is then processed (e.g. by the removal of introns) into messenger RNA and finally translated by ribosomes into protein. This process may be inhibited by the presence in the cell of "antisense RLNA". Therefore, as used herein, the term "antisense RNA" means an RNA sequence which is complementary to a sequence of bases in a RNA: complementary in the sense that each base (or a majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or lead to degradation of the mRNA, or have more than one of these effects. Such antisense RNA may be produced in the call by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes has been described, for example in European Patent Publication No 271988 to ICI. Reduction of gene expression has led to a change in the phenotype of the plant: either at the level of gross visible phenotypic difference e.g. lack of lycopene synthesis in the fruit of tomato leading to the production of yellow rather than red fruit or at a more subtle biochemical level e.g. change in the amount of polygalacturonase and reduction in depolymerisation of pectins during tomato fruit ripening (Smith et al, Nature, 334, 724–726, 1988, Smith et al, Plant Mol Biol 14, 369–380, 1990). Thus antisense RNA has been proven to be useful in achieving down-regulation of gene expression in plants.

An object of the present invention is to provide plants having an altered ability to synthesise lignin.

According to the present invention there is provided a recombinant DNA comprising a plant DNA having, in sequence a gene promoter sequence a coding region and a gene terminator, said coding region comprising a nucleotide sequence encoding a mRNA which is substantially homologous or complementary to mRNA encoded by an endogenous plant gene or a part thereof which encodes an enzyme essential to lignin biosynthesis, so that, when incorporated into a plant genome by transformation, mRNA transcribed from the said coding region inhibits production of the enzyme from the endogenous gene.

Preferably the coding region encodes mRNA in antisense orientation to the mRNA encoded by the said endogenous gene. Such an antisense sequence may be isolated from the untranscribed strand of the DNA encoding the said endogenous gene.

However, the coding region may alternatively be in the same orientation as the said endogenous gene. Such construction may lead to overproduction of the endogenous enzyme or it may inhibit production of same.

It is preferred that the coding region has a minimum size of 50 bases.

The target enzyme for controlling lignin production may be selected from the group consisting of cinnamyl alcohol dehydrogenase (CAD), cinnamoyl: CoA reductase (CCR) and catechol-O-methyl transferase (COMT).

The promoter may be selected from promoters known to operate in plants but is preferably selected from the group consisting of CaMV35s, GPAL2, GPAL3 and endogenous plant promoter controlling expression of the endogenous target enzyme, for example, the promoter of the CAD gene.

The invention also provides a method of inhibiting or altering lignin biosynthesis in a plant, comprising stably incorporating into the genome of the plant by transformation a recombinant DNA comprising a plant DNA having, in sequence a gene promoter sequence a coding region and a gene terminator, said coding region comprising a nucleotide sequence encoding a mRNA which is substantially homologous or complementary to mRNA needed by an endogenous plant gene or a part thereof which encodes an enzyme essential to lignin biosynthesis, so that, when incorporated into a plant genome by transformation, mRNA transcribed from the said coding region inhibits production of the enzyme from the endogenous gene.

Further, the invention provides a transformed plant possessing lower than normal ability to produce lignin characterised in that said plant has stably incorporated within its genome a recombinant DNA as described hereinabove. Examples of plants which may be so transformed are maize, eucalyptus, aspen, poplar, and tobacco. However, the invention is not restricted to these crops and it is envisaged that suitable primary applications will be in forage crops such as alfalfa, lolium and festuca. However, control of lignin synthesis has wide potential application in many crops.

The invention also provides the following sources of suitable genes for use in construction the recombinant DNAs:

(i) Plasmids pTCAD14 or pTCAD19 (tobacco CAD) which have been deposited, in *E. coli* strain XL1Blue host, at the National Collection of Industrial and Marine Bacteria, Aberdeen, United Kingdom, under the Accession Number 40404, on Apr. 17, 1991 and 40401 on Apr. 8, 1991 respectively.

(ii) Plasmid pZCAD1 (maize CAD) which has been deposited, in *E. coli* strain XL1Blue host, on Apr. 2, 1992 at the National Collection of industrial and Marine Bacteria, Aberdeen, United Kingdom, under the Accession Number 40501.

(iii) Plasmid pPOPCAD1 (poplar CAD) which has been deposited, in *E. coli* strain XL1Blue host, on Apr. 2, 1992 at the National Collection of Industrial and Marine Bacteria, Aberdeen, United Kingdom, under the Accession Number 40500.

(iv) Plasmid pEUCAD1 which has been deposited, in *E. coli* strain XL1Blue host, on Apr. 2, 1992 at the National Collection of Industrial and Marine Bacteria, Aberdeen, United Kingdom, under the Accession Number 40502.

These plasmids have been deposited under the provisions of the Budapest Treaty on the Deposit of Microorganisms for Patent Purposes.

Thus, the invention includes the DNA insert is contained in the clones pTCAD14, pTCAD19, pZCAD1, pPOPCAD1 and pEUCAD1 and variants thereof such as are permitted by the degeneracy of the genetic code or the functional equivalents thereof. In addition, the present invention provides a recombinant DNA construct containing the said DNA under control of a transcriptional control sequence operative in plants, so that the construct can generate mRNA in plant cells which can either be full-length or partial length in respect to the normal mRNA.

For the down-regulation of lignin synthesis the aforesaid DNA is in antisense or 'sense' orientation.

For the amplification of lignin biosynthesis the aforesaid DNA is in sense orientation thus to provide one or more additional copies of the said DNA in the plant genome. In this case the DNA is a full-length cDNA copy.

Thus, in a further aspect, the present invention provides DNA constructs comprising a transcriptional initiation region operative in plants positioned for transcription of a DNA sequence encoding RNA complementary to a substantial run of bases showing substantial homology to an mRNA encoding the protein produced by the gene in pTCAD14, pTCAD19, pZCAD1, pPOPCAD1 and pEUCAD1.

The invention further provides plant cells, and plants derived therefrom having stably incorporated in their genomes the aforesaid DNA in sense or antisense orientation, and fruit and needs of such plants.

The present invention is principally concerned with the suppression of lignin formation and, that being so, the inserted gene will be in antisense orientation, but there are instances where over-production of lignin may have an advantageous effect, for example to improve plant stalk strength, reduce plant stature and consequent lodging, and resistance to diseases, and the present invention provides means for achieving amplification of the lignin biosynthetic ability of plants.

Thus the invention relates generally to the regulation of the plant's lignin biosynthetic pathway, in which CAD plays a dominant role, in order that the production of CAD, and hence the production of lignin, may be increased, by supplying extra copies of the CAD gene which is the subject of this invention, or decreased by insertion of the CAD gene, or a portion thereof (usually of 50 or more bases), in antisense orientation so that the amount of CAD for catalysing lignin synthesis is reduced.

The constructs of the invention may be inserted into plants to regulate the production of the CAD enzyme. Depending on the nature of the construct, the production of the protein may be increased, or reduced, either throughout or at particular stages in the life of the plant. It is also possible to target the expression of the gene to specific cell types of the plant, such as the epidermis, the xylem, the roots etc.

The plants to which the present invention can be applied include commercially important food and forage plants, such as alfalfa, maize, oil aced rape, forage grasses and sunflower, and also tree crops such as eucalyptus, pine species and poplar.

DNA constructs according to the invention preferably comprise a sequence of at least 50 bases which is homologous to the DNA of the insert in pTCAD19 or pTCAD14. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

The preferred source of antisense RNA for use in the present invention is DNA derived from the clones pTCAD19 and pTCAD14. The required DNA encoding antisense RNA can be obtained in several ways! by cutting an appropriate sequence of DNA from pTCAD19 or pTCAD14 (or any other source of the CAD gene), by synthesizing a DNA fragment using synthetic oligonucleotides which are annealed and then ligated together in such a way an to give suitable restriction sites at each end; by using Synthetic oligonucleotides in a polymerase chain reaction (PCR) to generate the required fragment with suitable restriction sites at each end. The DNA is then cloned into a vector containing upstream promoter and downstream terminator sequences, the cloning being carried out so that the DNA sequence is inverted with respect to its orientation to the promoter in the strand from which it was cut. In the new vector, the strand that was formerly the template strand becomes the coding strand, and vice versa. The new vector will thus encode RNA in a base sequence which is complementary to the sequence of pTCAD19 and pTCAD14 mRNAS. Thus the two RNA strands are complementary not only in their base sequence but also in their orientations (5' to 3').

As source of the DNA bass sequence for transcription, it is convenient to use a cDNA clone such as pTCAD19 and pTCAD14. The base sequence of pTCAD19 is set out in FIG. 3 and the sequence of pTCAD14 is shown in FIG. 4.

A source of DNA for the base sequence for transcription is the promoter of the CAD gene itself or other genes involved in lignification such as the promoter of the phenylalanine ammonia lyase gene or its modified version which permits expression in xylem tissue. Such a gene may differ from the cDNA of pTCAD19 or pTCAD14 in that introns may be present. The introns are not transcribed into mRNA (or, if so transcribed, are subsequently cut out). When using such a gene as the source of the base sequence for transcription it is possible to use either intron or exon regions.

A further way of obtaining a suitable DNA base sequence for transcription is to synthesize it ab initio from the appropriate bases. Recombinant DNA and vectors according to the present invention may be made as follows. A suitable vector containing the desired base sequence for transcription (for example pTCAD19) is treated with restriction enzymes to cut out the sequence. The DNA strand so obtained is cloned (in reverse orientation) into a second vector containing the desired promoter sequence (for example cauliflower mosaic virus 35s RNA promoter or the bean PAL promoter, Bevan et al, EMBO J.8, 1899–1906 1988) and the desired terminator sequence (for example the 3' of the *Agrobacterium tumefaciens* nopaline synthase gene.

According to the invention we propose to use both constitutive promoters (such as cauliflower mosaic virus 35s RNA) and inducible or developmentally regulated promoters (such as the PAL gene promoter or the endogenous CAD gene promoter) as circumstances require. Use of a constitutive promoter will tend to affect functions in all parts of the plant: while by using a tissue specific promoter, functions may be controlled more selectively. The use of a tissue-specific promoter, has the advantage that the antisense or sense RNA is only produced in the tissue in which its action is required.

Vectors according to the invention may be used to transform plants as desired, to make plants according to the invention. Dicotyledonous plants, such as alfalfa, oil seed rape etc, may be transformed by Agrobacterium Ti plasmid technology, for example as described by Bevan (1984) Nucleic Acid Research, 12, 8711–8721. such transformed plants may be replicated sexually, or by cell or tissue culture.

The degree of production of RNA in the plant cells can be controlled by suitable choice of promoter sequences, or by selecting the number of copies or the site of integration, of the DNA sequences according to the invention that are introduced into the plant genome. In this way it may be possible to modify lignification to a greater or lesser extent.

The constructs of our invention may be used to transform calls of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants. Examples of genetically modified plants according to the present invention include, alfalfa, oil seed rape, sunflower, sorghum, maize, festuca, and trees such as eucalyptus, poplar, and pine.

In the present invention, we use antisense RNA in order to determine the phenotype of transgenic plants which show modified, that is increased or reduced, expression of pTCAD19 or pTCAD14 by the use of antisense and sense expression vectors.

Figure 6:
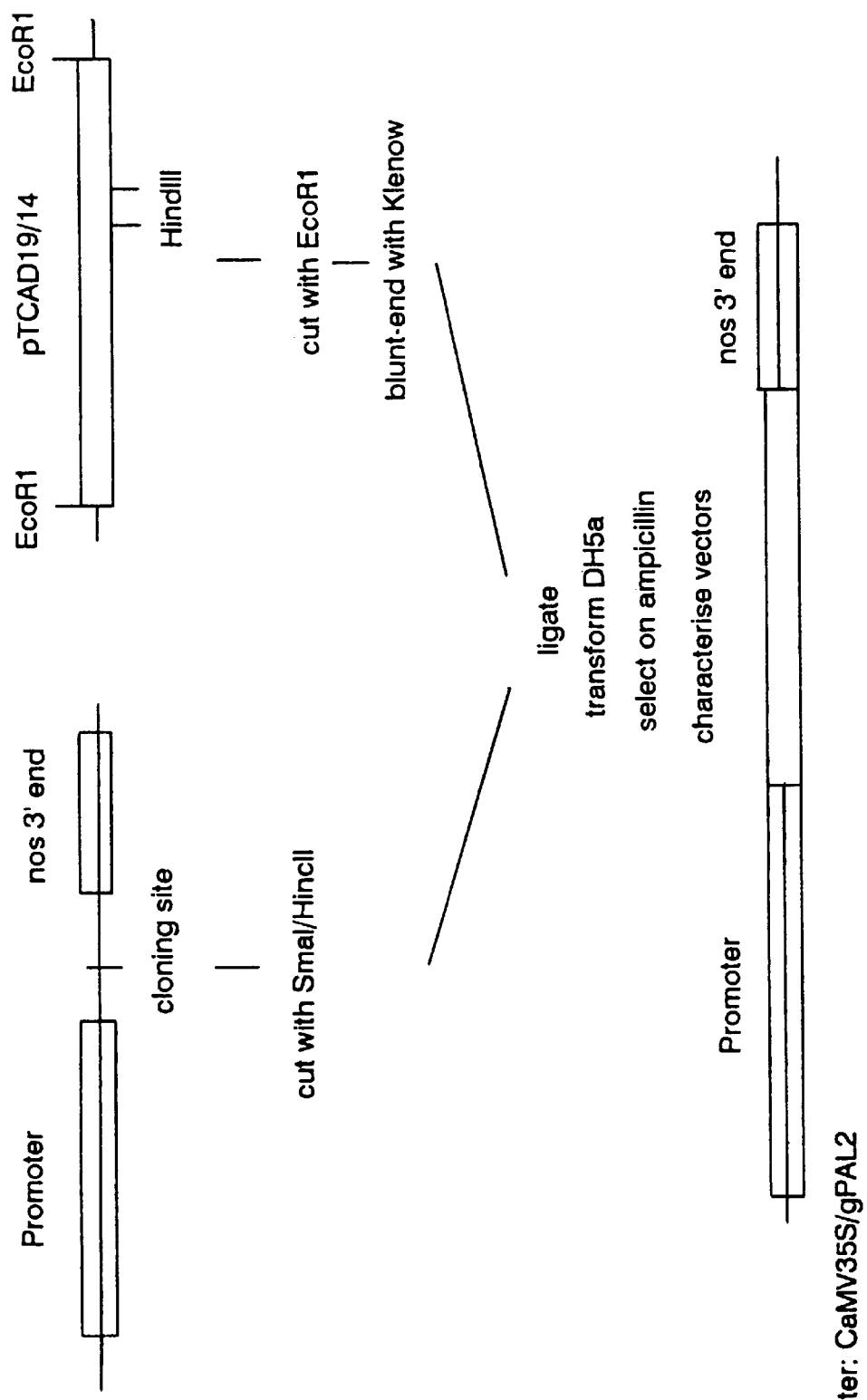

The invention will now be described further with reference to the accompanying drawings, in which:

FIG. 1 shows the partial amino acid sequence determined from purified tobacco CAD protein (SEQ ID NO: 1–SEQ ID NO: 15), FIG. 2 shows the design of the oligonucleotide sequence used to identify a CAD clone (SEQ ID NO: 16), FIG. 3 shows the complete sequence of pTCAD19 (SEQ ID NO: 17), FIG. 4 shows the sequence of pTCAD14 tobacco cDNA clone (SEQ ID NO: 18), FIG. 5 shows the construction of antisense and sense vectors using the ECoR1-HindIII fragment of pTCAD19/pTCAD14, FIG. 6 shows the construction of expression vectors containing the complete tobacco CAD cDNA clones, FIG. 7 shown the complete sequence of pPOPCAD1 (SEQ ID NO: 19), FIG. 8 shows the complete sequence of pEUCAD1 (SEQ ID NO: 20), FIG. 9 shows sequence of primers used to generate a maize CAD clone by PCR (SEQ ID NO: 21 and SEQ ID NO: 22), and, FIG. 10 shows the sequence of pZCAD1, a 200 bp PCR product from maize genomic DNA (SEQ ID NO: 23), FIG. 11 shows CAD activities of the control and antisense plants.

The invention will now be described, by way of illustration, in the following examples.

EXAMPLE 1

Development of an efficient purification protocol for CAD enzyme

Improved protocols have been developed for the purification or CAD. The new procedure is simpler than the previously published methods and is based on the following steps:

1.Preparation of tobacco stem extract by homogenization and 70–40% ammonium sulphate precipitation.

Six week old tobacco stems were frozen in liquid N, crushed with a hammer and homogenized in a Waring blender in buffer A. The homogenate was centrifuged at 45000×g for 30 min. Solid ammonium sulphate was added to the supernatant to bring it to 70% saturation and proteins were precipitated at 4° C. for 30 min. The precipitate was collected by centrifugation at 10,000 rpm for 1 hour. The pellet was resuspended in a minimum volume of buffer supplemented with 5% ethylene glycol, to reduce the ammonium sulphate concentration to approximately 40% saturation. Material that did not resuspend was removed by centrifugation.

2. Affinity chromatography on Blue Sepharose.

The supernatant was desalted and applied to a Blue Sepharose column. The column was washed in at least 6 column volumes buffer including one column volume supplemented with 4 mM NAD. This wash elutes other alcohol dehydrogenases. Specific elution of CAD was performed with a gradient of 0–4 mM NADP in buffer B. CAD-containing fractions were pooled and 5% ethylene glycol was added.

3. Ion exchange FPLC on Mono Q.

The pooled fractions from Blue Sepharose were applied to an FPLC Mono Q column. The column was washed until the Absorbance dropped to baseline levels. Proteins were eluted in a linear gradient of buffer with 20–400 mM Tris-HCl, pH 7.5.

4. Affinity chromatography on 2'5' ADP Sepharose.

MonoQ fractions were applied to a column of 2'5'ADP-Sepharose. The column was washed with 6 column volumes buffer including one column volume supplemented with 4 mM NAD. Specific elution was performed in a linear gradient of buffer with 0–4 mM NADP.

Using this protocol tobacco CAD was purified to homogeneity. 600 μg were obtained from 4 Kg material representing 0.05% total soluble protein. This represents a purification of approximately 2000 fold. The purified enzyme has a specific activity of 173 nKat/mg protein. The pure enzyme is specific for NADP and exhibits a Km for coniferyl alcohol of 12 μmol/l.

EXAMPLE 2

Characterisation of CAD enzyme

Purified CAD consists of two subunits of approximate molecular weights 42.5 kDa and 44 kDa. When slices isolated separately from native gels containing the CAD protein (identified as two separate bands by silver staining) were transferred to and run on an SDS gel, each native form appears to contain both polypeptides. Pure protein was run on a reverse phase HPLC column, yielding two well separated protein peaks probably the two polypeptides. Peptide mapping of each polypeptide with N-chlorosuccinimide/urea and amino acid analysis of purified subunits suggest that they are very similar.

Both peptides were digested with trypsin and the sequence of the resulting fragments was determined. The sequence of the peptides is shown in FIG. 1.

This shows clearly that CAD is represented by two closely related polypeptides.

EXAMPLE 3

Establishment of a stem-specific cDNA library from tobacco

A cDNA library has been generated using RN extracted from six week old tobacco stems. 20 ug of polyA RNA was prepared and cDNA synthesised. Part of this was cloned into lambda-ZAP II vector (a commercially available cloning vector). This yielded 860,000 recombinants, 70% of which have inserts of 1 Kb or greater, as determined by PCR on 24 randomly selected clones.

EXAMPLE 4

Identification of a CAD cDNA 600,000 recombinants were screened using an oligonucleotide probe (CAD116) shown in FIG. 2. This oligo was designed against peptide sequence 4 from FIG. 1.

One strongly hybridizing clone was identified, purified and characterised. This clone, pTCAD19, has a cDNA insert of 1419 bp. Analysis of the DNA sequence-derived amino acid sequence clearly demonstrates that it represents a CAD clone as several regions show DNA sequence-derived amino acid sequences identical to the peptide sequences found in FIG. 1 representing the 42.5 kDa peptide (peak 2 from RHPLC).

EXAMPLE 5

Rescreening of the tobacco cDNA library with the insert of pTCAD19.

The 600,000 clones representing the tobacco stem cDNA library was rescreened using the EcoR1 insert of pTCAD19. Five additional clones were identified, purified and characterized.

Sequencing of these clones has allowed identification of two cDNA clones which are different from PTCAD19, encoding the peptide found in peak 1 from RHPLC. A representative clone is called pTCAD14 and its sequence is shown in FIG. 5. This demonstrates that this clone is different from pTCAD19 and that it contains peptide sequence derived from the peak 1 protein.

EXAMPLE 6

Generation ot CAD antisense vectors

A. Vectors Based on pJR1 pTCAD19 and pTCAD14 were cut with EcoR1 and HindIII, and the resulting fragments of 981 bases were isolated by agarose gel electrophoresis. The fragment was made blunt ended using Klenow fragment A. The fragment was then cloned into pJR1 cut with Sma1. Clones containing the insert in the antisense orientation are called pJT19A and pJT14A. Clones which contain the fragment in sense orientation are called pJT19S and pJT19S. The construction of these vectors is shown in FIG. 5.

B. Vectors Based on pMK4 pTCAD19 was cut with EcoR1 and HindIII, and the resulting fragment of 981 bases was isolated by agarose gel electrophoresis. The fragment was made blunt ended using Klenow fragment A. The fragment was then cloned into pMK4 cut with HindIII. pMK4 is an expression vector which contains the Dral fragment of the bean phenylelanine ammonia lyase promoter, a multiple cloning site and the nos 3' end. Clones containing the insert in the antisense orientation are called pKT19A and pMT14A. Clones which contain the fragment in sense orientation are called pMT19S and pMT14S. The construction of these vectors is shown in FIG. 5.

EXAMPLE 7

Generation of CAD expression vectors

The complete insert of pTCAD19 was excised by restriction of the plasmids with EcoR1. The inserts were made blunt ended and cloned into pJR1 and pMK4. The resulting vectors are called:

pJR1 based:

pJT19FS and pJT14FS (sense)

pJT19FA and pJT14FA (antisense)

pME4 based, pHT19FS and pMT14FS (sense)

pMT29FA and pMT14FA (antisense)

The construction of these vectors is shown in FIG. 6.

EXAMPLE 9

Transformation of tobacco using vectors described in this application (a) Transfer of Vectors to Agrobacterium The antisense and sense constructs were introduced into A. tumefaciens LBA4404 by direct transformation following published procedures.

The presence and integrity of the antisense constructs were checked by restriction digestion and Southern blot experiments to check that no recombination had occured during the transfer of the vectors to Agrobacterium.

b) Tobacco Leaf Disc Transformation

Tobacco (*N. tabaccum*, variety *Samsum*) leaf discs were transformed using wall established previously published procedures. Plants containing the CAD antisense construct were identified by PCR and selected for further analysis.

EXAMPLE 10

Analysis of transformed plants a) CAD Enzyme Measurements on Tissue from Transformed Plants Plant material was used from both transformed and untransformed control plants for CAD enzyme determinations. Stem material was ground with CAD extraction buffer containing 200 MM Tris/HCl pH 7.5, 0.5% (v/v) PEG 6000, 5% (w/V) PVP, and 15 m β-mercaptoethanol (500 μl). The crude homogenate was centrifuged and the supernatant used as source of enzyme. The assay reaction contained 10 mM coniferyl alcohol (50 μl), 10 MM NADP+(50 μl), 100 mM Tris/HCl pH 8.8 (800 μl). This was incubated at 30° C. for 10 minutes, then enzyme extract (100 μl) was added and the whole mixture incubated for a further 10 minutes at 30° C. The OD400 was recorded against a blank supplemented with water. One sample was taken from each plant. Assays were conducted in duplicate. The results of the analysis of these enzyme measurement are shown in FIG. 11. This clearly indicates that the transgenic plants exhibit a wide range of CAD enzyme activities. Plants with lowest levels of CAD activity show approximately 10% of control CAD enzyme values.

b) Polymerase Chain Reaction to determine presence of antisense genes

DNA was extracted from selected plants. Oligonucleotides to sequences in the CaMV or PAL promoter and nos 3' terminator were used as primers in the polymerase chain reaction (PCR). To confirm that these products were CAD sequences, a Southern blot of these products was probed with a third oligonucleotide representing CAD sequences. This analysis demonstrated that all plants used for the analysis shown in FIG. 10 contained the antisense constructs.

Plants with low CAD activity were backcrossed and selfed. Progeny plants were analysed in detail for the heritability of the CAD antisense gene and the low CD enzyme phenotype. This indicates that the low CAD phenotype segregates with the antigens* gene.

EXAMPLE 11

Isolation of a cDNA clone encoding poplar CAD.

80,000 colonies from a poplar cDNA library constructed in pUC18 were probed with the entire EcoR1 insert from pTCAD19. Hybridization was performed in 3×SSC, 0.5% milk powder at 60° C. Washing was performed in 3×SSC, 0.5% SDS at 60° C. for 3×0.5 hour. One clone was isolated, named pPOPCAD1. This clone contained an insert of 1376 bp and was 70% homologous to pTCAD19. The sequence of pPOPCAD1 is shown in FIG. 7.

EXAMPLE 12 construction of sense/antisense vectors.

The invert of pPOPCAD1 was exised as a BamHI fragment and cloned into the plant expression vector pGSJ780A in the antisense and sense orientations. These vectors were used to transform poplar and open.

EXAMPLE 13

Establishment of a cDNA library from Eucalyptus

A cDNA library was generated using RNA extracted from 7 days old cell suspension cultures of *Eucalyptus gunnii* (clone 832, Afocel). 5 μg of polyA+ RNA was prepared and used to synthesize cDNA. This was cloned into the EcoRI site of lambda gt11 (a commercially available cloning vector). his yielded $10^6$ recombinants, 60% of which have inserts of 1 kb or greater, as determined by PCR on 24 randomly selected clones.

EXAMPLE 14

Functional identification of the eucalyptus CAD clone

The identity of the eucalyptus CAD clone was confirmed by the expression of catalytically active CAD enzyme in a transformed *E. coli* bacterial host. This was achieved by cloning the eucalyptus CAD cDNA in the expression vector pT7—7 as described by Tabor and Richardson, Proceedings of the National Academy of Science 82, 1985, transforming the commercially available *E. coli* lysogenic strain BL21, inducing the expression of the cloned gene under control of the T7 promoter with IPTG and assaying the whole cell extract for CAD activity. The results unequivocally identified the clone as specifying the enzyme CAD.

EXAMPLE 15

Cloning and characterization of a Eucalyptus CAD clone 600,00 recombinants from the amplified library (1.6 $10^6$ recombinants) were screened using the EcoRI insert of pTCAD19. Six positive clones were plaque purified; the largest has been subcloned into pGEN3 (a commercially available cloning vector), characterised and sequenced. This full length clone (1391 bp) encodes a protein of 356 amino acids which has a very high homology with the sequence of the tobacco CAD (76.4% of the amino acids are identical, 11% are well conserved).

The sequence of this clone, pEUCAD1 is shown in FIG. 8.

EXAMPLE 16

Cloning of a partial CAD clone from maize

PCR primers derived from sequences highly conserved between pTCAD19 and pPOPCAD1 (FIG. 9) were used under suitable conditions to generate a PCR product from maize genomic DNA. The product was cloned into Bluescript SK+/− and its nucleotide sequence determined (FIG. 10). This clone was clearly identified as encoding part of the maize CAD gene by DNA sequence comparison to the tobacco CAD sequences of pTCAD14/19.

EXAMPLE 17

Analysis of call wall bound and soluble phenolics in tobacco transformed with antisense tobacco CAD CAD is believed to play a key role in the regulation of lignin biosynthesis and this Example reports confirmation of the effect of lignin down-regulation in transformants containing the antisense gene to CAD.

Lignin is known to react with thioglycolic acid (TGA) (Freudenberg et.al. in "Constitution and Biosynthetic of Lignin", Springer Verlag, Berlin, 1968) and methods employing TGA lignin extraction have been employed in the pest to determine the amount of lignins present in plants after wounding. However, simple TGA extraction does tend to overestimate the amount of lignin because certain other components of the plant tissue are co-extracted. The simple method may be adapted to include a step of first saponifying the methanol insoluble component of the cell wall prior to TGA extraction (Campbell & Ellis, Phytochem 31: 737 (2992)).

Stem sections (5 cm) from eight week old the sample plants were lyohilised and separated into "green tissue" comprising the phloem, cortex and epidermis and "woody tissue" comprising the xylem and pith.

Ten samples each of control and transformed plants were analysed blind for TGA extractable cell wall complexes by the method described by Campbell and Ellis and also for the phenolics content of methanol and alkali extracts by the methods generally described by Ferraris et.al. J. Disease Protect. 94; 624 (1987).

The results are reported in Tables 1, 2, and 3 below.

TABLE 1

Direct numerical comparison of the content of TGA extractable complexes obtained from lyophilised stem tissue from control and transformed plants

| Tissue | Control Plants (C) | Transformed Plants (T) | Ratio T/C |
|---|---|---|---|
| green | 0.03 (0.01) | 0.05 (0.02) | 1.53 |
| woody | 0.22 (0.05) | 0.37 (0.12) | 1.60 |
| total | 0.26 (0.06) | 0.42 (0.13) | 1.59 |

The units are A280/mg dry weight with the standard errors in parentheses

TABLE 2

Direct numerical comparison of the content of methanol-extractable phenolics obtained from lyophilised stem tissue from control and transformed plants

| Tissue | Control Plants (C) | Transformed Plants (T) | Ratio T/C |
|---|---|---|---|
| green | 4.37 (0.58) | 5.64 (0.76) | 1.28 |
| woody | 0.81 (0.12) | 1.39 (0.33) | 1.72 |
| total | 5.18 (0.65) | 7.03 (0.92) | 1.35 |

The units are $\mu$g of ferulate equivalents per mg of dry weight with the standard errors shown in parentheses.

TABLE 3

Direct numerical comparison of the content of alakali-extractable phenolics obtained from lyophilised stem tissue from control and transformed plants

| Tissue | Control Plants (C) | Transformed Plants (T) | Ratio T/C |
|---|---|---|---|
| green | 1.29 (0.32) | 2.13 (0.52) | 1.65 |
| woody | 0.82 (0.17) | 2.92 (1.59) | 3.58 |
| total | 2.10 (0.46) | 5.06 (2.06) | 2.4 |

The units are $\mu$g of ferulate equivalents per ag of dry weight with the standard errors shown in parentheses.

Although the results in Table 3 show an increase in the amount of TGA-extractable complexes in the CAD-antisense plants the increase can be explained by the suggestion that the chemical composition has altered and this would not entirely be surprising since the inhibition of CAD would inhibit synthesis of the type lignin polymers which are normally synthesised downstream of the CAD catalysed stop in the pathway and result in a build-up of the upstream phenolic acid precursors.

This change in the character of the lignin was confirmed by comparing the uv spectra of the TGA complexes from the control and transformed plants. Further confirmation has been obtained by alkaline nitrobenzene oxidation analysis which has revealed the presence of additional components in the transformed plants and chromatographic analysis indicates that these are phenolic acids.

Thus the TGA extraction analysis indicates that down-regulation of CAD makes the "lignin" more amenable to removal and this property should be reflected in facilitation of cellulose extraction processes.

The same feature is also indicated by the analyses reported in Tables 2 and 3. The alkaline extraction is further significant in that it is common farming practice to store forage crops as silage and this frequently involves addition of alkali (ammonia, usually) and it may be expected that silage made from forage crops tranformed with CAD antisense will have lower than normal lignin concentration, leading to improved digestibility.

What is claimed is:

1. A method of altering the content or composition of lignin in a plant, comprising stably incorporating into the genome of the plant by transformation a recombinant DNA comprising a gene promoter sequence and a gene terminator, and an interposed region comprising a nucleotide sequence encoding a mRNA which on translation produces cinnamyl alcohol dehydrogenase.

2. A recombinant DNA comprising a gene promoter sequence and a gene terminator, and an interposed region comprising a nucleotide sequence encoding a mRNA which on translation produces cinnamyl alcohol dehydrogenase.

3. A recombinant DNA as claimed in claim 1 in which said gene promoter is selected from the group consisting of CaMV35S, GPAL2, GPAL3 and endogenous plant promoters controlling expression of the endogenous CAD gene.

4. The method of claim 1 wherein the gene is a CAD gene.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Xaa Xaa Leu Xaa Val
1               5

(2) INFORMATION FOR SEQ ID NO:2:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Xaa Xaa Leu Xaa Val
1               5

(2) INFORMATION FOR SEQ ID NO:3:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Thr Thr Ile Gly Xaa Ala Ala Ile Val Lys
1               5                   10

(2) INFORMATION FOR SEQ ID NO:4:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Thr Ala Ile Gly Ala Ala Ile Val
1               5

(2) INFORMATION FOR SEQ ID NO:5:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Phe Pro Ser Asp Val Leu Arg Pro Tyr Thr Tyr Thr Leu Asp
1               5                   10

(2) INFORMATION FOR SEQ ID NO:6:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Pro Ser Gly Leu Leu Ser Pro Tyr Thr Tyr Thr Leu Val
1               5                   10

(2) INFORMATION FOR SEQ ID NO:7:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Phe Val Val Asp Val Ile Gly Lys
1               5

(2) INFORMATION FOR SEQ ID NO:8:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Phe Val Val Asp Val Ala Gly Asp
1               5

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Met Asp Tyr Ile Asn Gly Ala Met Glu Arg
1               5                   10

(2) INFORMATION FOR SEQ ID NO:10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Asp Tyr Ile Asn Thr Ala Met Xaa
1               5

(2) INFORMATION FOR SEQ ID NO:11:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Arg Thr Leu Gly Met Ser Asn
1               5

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Asn Asp Leu Gly Met Ser Asn Tyr Pro
1           5

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Ala Met Gly Xaa Xaa Val Xaa Val Ile
1           5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Ala Xaa Thr Pro Tyr Phe Xaa
1           5

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Ser Gly Ile Leu Gly Leu
1           5

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

ATGGAYTAYA THAAYGGNGC NATGGA                26

(2) INFORMATION FOR SEQ ID NO:17:

(i) SEQUENCE CHARACTERISTICS:
        (A) LENGTH: 1419 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
ATTTCTTTCT CTTTCCCTTG AACTGTGTTT TCATTTTTTC TGCTCTGAAA CAATAGTGTT      60

TTCCTTGTAG ATTTTAAGTT AAAAGAAAAC CATGGGTAGC TTGGATGTTG AAAAATCAGC     120

TATTGGTTGG GCTGCTAGAG ACCCTTCTGG TCTACTTTCA CCTTATACCT ATACTCTCAG     180

AAACACAGGA CCTGAAGATG TGCAAGTCAA AGTTTTGTAT TGTGGACTTT GCCACAGTGA     240

TCTTCACCAA GTTAAAAATG ATCTTGGCAT GTCCAACTAC CCTCTGGTTC CTGGACATGA     300

AGTGGTGGGA AAAGTAGTGG AGGTAGGAGC AGATGTGTCA AAATTCAAAG TGGGGACAC      360

AGTTGGAGTT GGATTACTCG TTGGAAGTTG TAGGAACTGT GGCCCTTGCA AGAGAGAAAT     420

AGAGCAATAT TGCAACAAGA AGATTTGGAA TTGCAATGAT GTCTACACTG ATGGCAAACC     480

CACCCAAGGT GGTTTTGCTA ATTCTATGGT TGTTGATCAA AACTTTGTGG TGAAAATTCC     540

AGAGGGTATG GCACCAGAAC AAGCAGCACC TCTATTATGT GCTGGCATAA CAGTATACAG     600

TCCATTCAAC CATTTTGGTT TTAATCAGAG TGGATTTAGA GGAGGAATTT TGGGATTAGG     660

AGGAGTTGGA CATATGGGAG TGAAAATAGC AAAGGCAATG GGACATCATG TTACTGTCAT     720

TAGTTCTTCA AATAAGAAGA GACAAGAGGC ATTGGAACAT CTTGGTGCAG ATGATTATCT     780

TGTTAGTTCA GACACTGATA AAATGCAAGA AGCTGCTGAT TCACTTGACT ATATTATTGA     840

TACTGTCCCT GTTGGCCATC CTCTTGAACT TTATCTTTCT TTGCTTAAAA TTGATGGCAA     900

ACTTATCTTG ATCGGAGTTA TCAACACCCC CTTGCAATTT ATCTCTCCCA TGGTTATGCT     960

CGGGAGAAAG AGCATCACTG GAAGCTTTAT TGGTAGCATG AAGGAAACAG AGGAAATGCT    1020

AGACTTCTGC AAAGAGAAAG GTGTGACTTC ACAGATTGAG ATAGTGAAAA TGGATTATAT    1080

CAACACTGCA ATGGAGAGGT TGGAGAAAAA TGATGTGAGC TACAGATTTG TTGTTGATGT    1140

TGCTGGAAGC AAGCTTGACC AGTAATTGCA CAAGAAAAAC AACATGGAAT GGTTCACTAT    1200

TATACAACAA GGCTATGAGA AAAATAGTAC TCCTCAACTT TGATGTCATC TTTGTTACCT    1260

TTGTTTTATT TTCCACCTGT ATTATCATAT TTGGTGGTCG AGAGTGACGT TTATGTATAT    1320

TTTCTTTCTT CAAAACAATC TTAAATGAAT TTGGATGTTG GTGACGATTT TGAAATATAC    1380

CAACCATGCA AACTTACTTT GGTAGAAAAA AAAAAAAAA                           1419
```

(2) INFORMATION FOR SEQ ID NO:18:

(i) SEQUENCE CHARACTERISTICS:
        (A) LENGTH: 1393 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
TCTTTCCCTT GAACTGTGTT TTCGTTTTTT CTGCTCTAAA ACAATCGTGT GTTCCTTGTA      60

GATTTTAAGT TTAAAGAACA TCATGGGTGG CTTGGAAGTT GAGAAAACAA CTATTGGTGG     120

GGCTGCTAGA GACCCTTCTG GTGTACTTTC ACCTTATACC TATACTCTCA GAAACACAGG     180
```

```
ACCTGAAGAT GTGGAAGTCA AAGTTTTGTA TTGTGGGCTC TGTCACACTG ATCTTCACCA      240

AGTTAAAAAT GATCTTGGCA TGTCCAACTA CCCTCTGGTT CCTGGACATG AAGTGGTGGG      300

AGAAGTGGTG GAGGTAGGAC CAGATGTGTC AAAATTCAAA GTTGGGGACA CAGTTGGAGT      360

TGGATTACTC GTTGGAAGTT GCAGGAACTG TGGCCCTTGC AAGAGAGATA TAGAGCAATA      420

TTGCAACAAG AAGATTTGGA ACTGCAATGA TGTCTACACT GATGGCAAAC CCACCCAAGG      480

TGGTTTTGCT AAATCCATGG TTGTTGATCA AAAGTTTGTG GTGAAAATTC CAGAGGGTAT      540

GGCACCAGAA CAAGCAGCAC CTCTATTATG TGCTGGTATA ACAGTATACA GTCCATTGAA      600

CCATTTTGGT TTCAAACAGA GTGGATTAAG AGGAGGAATT TTGGGATTAG GAGGAGTGGG      660

ACACATGGGA GTGAAAATAG CAAAGGCAAT GGGACATCAT GTTACTGTCA TTAGTTCTTT      720

AAATAAGAAG AGACAAGAGG CATTGGAACA TCTTGGTGCA GATGATTATC TTGTCAGTTC      780

AGACACTGAT AAAATGCAAG AGGCTTCTGA TTCACTTGAC TATATTATTG ATACTGTCCC      840

TGTTGGCCAT CCTCTTGAAC CTTATCTTTC TTTGCTTAAA ATTGATGGCA AACTTATCTT      900

GATGGGAGTT ATCAACACCC CCTTGCAATT TATCTCCCCC ATGGTTATGC TCGGAGAAAA      960

GAGCATCACA GGAAGCTTTA TTGGTAGCAT GAAGGAAACA GAGGAAATGC TAGATTTCTG     1020

CAAAGAGAAA GGTGTGACTT CACAGATTGA GATAGTGAAA ATGGATTATA TCAACACTGC     1080

AATGGAGAGG TTGGAGAAAA ATGATGTGAG GTACAGATTT GTGGTTGATG TTATTGGAAG     1140

CAAGCTTGAC CAGTAATTAT ATTACACAAG AAAAACAACA TGGAATGGTT CACTATTATA     1200

CAAGGCTGTG AGAATACTAA ACTTTGATGT CGTCTTTTGT ATCCTTTTGT TTTATTTGCC     1260

ACCTGTATTT TCTTATTTGG TGATCGAGAG TGACGTTTAT GTATTATTTT CTTTCTTCAA     1320

AACAATTTAA TGTATGAATT TGGATGTTGG TGAAAAAAAA AAAAAAAAAA AAAAAAAAA      1380

AAAAAAAAAA AAA                                                         1393

(2) INFORMATION FOR SEQ ID NO:19:

(i) SEQUENCE CHARACTERISTICS:
        (A) LENGTH: 1283 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CTCTCTTAGC CTCATTGTTT CAAGAAAATG GGTAGCCTTG AAACAGAGAG AAAAATTGTA       60

GGATGGGCAG CAACAGACTC AACTGGGCAT CTCGCTCCTT ACACCTATAG TCTCAGAGAT      120

ACGGGGCCAG AAGATGTTTT TATCAAGGTT ATCAGTTGTG GAGTTTGCCA TACCGATATC      180

CACCAAATCA AAAATGATCT TGGCATGTCA CACTATCCTA TGGTCCCTGG CCATGAAGTG      240

GTTGGTGAGG TTGTTGAGGT GGGATCAGAT GTGACAAGGT TCAAAGTTGG AGATGTTGTC      300

GGTGTTGGAG TCATCGTTGG AAGCTGCAAG AATTGTCATC CATGCAAATC AGAGATTGAG      360

CAATACTGCA ACAAGAAAAT CTGGTCTTAC AATGATGTCT ACACTGATGG CAAACCCACC      420

CAAGGAGGCT TGCTGAATC CATGGTTGTG CATCAAAAGT TTGTGGTGAG AATTCCTGAT      480

GGGATGTCAC CAGAACAAGC AGCGCCGCTA TTGTGCGCTG GATTGACAGT TTACAGCCCA      540

CTTAAACACT TTGGACTGAA ACAGAGTGGG CTAAGAGGAG GGATTTTAGG ACTTGGAGGA      600

GTAGGGCACA TGGGGGTGAA GATAGCAAAG GCAATGGGAC ACCATGTAAC TGTGATTAGT      660

TCTTCTGACA AGAAGCGGGA GGAGGCTATG GAACATCTTG GTGCTGATGA ATACTTGGTC      720
```

-continued

```
AGCTCGGATG TGGAAAGCAT GCAAAAAGCT GCTGATCAAC TTGATTATAT CATCGATACT      780

GTGCCTGTGG TTCACCCTCT GGAGCCTTAC CTTTCTCTGT TGAAACTTGA TGGCAAGCTG      840

ATCTTGATGG GTGTTATTAA TGCCCCATTG CAGTTTGTTA CGCCTATGGT TATGCTTGGG      900

AGAAAGTCTA TCACCGGGAG CTTCATAGGG AGCATGAAGG AGACAGAGGA GATGCTTGAG      960

TTCTGCAAGG AAAAGGGAGT GGCCTCCATG ATTGAAGTGA TCAAAATGGA TTATATCAAC     1020

ACGCATTCGA GAGGCTTGAG AAAAATGATG TGAGATATAG ATTCGTTGTC GATGTTGCTG     1080

GTAGCAAGCT TATTCACTGA ACAACAATAC TCTTCATATT CGAAAAAAAA ACGATATACA     1140

TTGATACCTG TTTCAGACGT GACTTTATTT CCGAGTGATG TGTTTTGTGG ATCAAATGTG     1200

ACAGTGTGTC TTTGCTTTTA AAATAAAGAA AAGGTTGAAT TGTTTTTTTA AAAAAAAAAA     1260

AAAAAAAAAA AAAAAAAAA AAA                                              1283
```

(2) INFORMATION FOR SEQ ID NO:20:

(i) SEQUENCE CHARACTERISTICS:
        (A) LENGTH: 1377 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
CTGCTCCTAC CCGCAACTTC CCATCTACAT AAGCAGCAAG TTTACGGCTC TGTCGAATCT       60

CTCTCCGAGC ACCACTTTGA AGAAGCTTG GATCTTTGAG CAAAAATGGG CAGTCTTGAG       120

AAGGAGAGGA CCACCACGGG TTGGGCTGCA AGGGACCCGT CTGGCGTTCT CTCTCCTTAC      180

ACTTATAGCC TCAGAAACAC GGGACCAGAA GATCTTTACA TCAAGGTGTT GAGCTGCGGA      240

GTTTGCCACA GTGACATTCA CCAGATCAAG AATGATCTTG GCATGTCCCA CTACCCTATG      300

GTTCCTGGGC ATGAAGTGGT GGGCGAGGTT CTGGAGGTGG ATCAGAGGT GACAAAGTAC       360

AGAGTTGGTG ACCGAGTGGG AACCGGTATA GTGGTTGGGT GCTGCAGAAG CTGTAGCCCT      420

TGCAATTCGG ACCAGGAGCA ATATTGCAAC AAGAAGATTT GGAATTACAA TGACGTGTAC      480

ACCGATGGCA AGCCCACTCA AGGTGGGTTT GCTGGTGAGA TAGTGGTTGG CGAAAGGTTT      540

GTGGTGAAAA TCCCAGATGG GTTAGAGTCG GAACAGGCAG CGCCGCTGAT GTGCGCTGGT      600

GTGACCGTGT ACAGCCCTCT GGTGCGCTTT GGGCTCAAGC AAAGCGGGTT GAGAGGAGGG      660

ATATTGGGGC TTGGAGGGGT TGGCCACATG GGGGTGAAGA TAGCCAAGGC CATGGGACAC      720

CACGTGACTG TGATAAGCTC TTCTGATAAG AAGAGAACGG AGGCATTGGA GCACCTGGGT      780

GCCGATGCTT ACCTAGTGAG CTCCGATGAA AATGGAATGA AAGAGGCCAC TGATTCTCTC      840

GACTACATTT TTGACACTAT CCCTGTGGTT CACCCTCTCG AACCTTACCT GGCCTTGTTG      900

AAGCTCGATG GAAAGCTGAT CTTGACTGGT GTCATCAATG CTCCTCTTCA ATTTATCTCT      960

CCCATGGTTA TGCTTGGGAG GAAGTCAATC ACTGGGAGTT TCATAGGGAG CATGAAGGAA     1020

ACAGAGGAGA TGCTTGAGTT CTGCAAAGAA AAGGGATTGA CTTCCCAGAT CGAAGTGATC     1080

AAGATGGATT ATGTCAACAC CGCCCTAGAG AGGCTCGAGA AGAATGATGT CAGGTACAGG     1140

TTCGTCGTGG ACGTCGTGGG AAGCAAGCTT GATTAGTTTC GGCTTTCCCC ATAAGTAAAC     1200

AAGAAATCGA CTTGCTTGTC TCTCAATTCG AGTTCCTCAT GCCCTCTGTT GTATCATTGT     1260

TTGTTATACC GAGAGTGCTA TTTTCTTCTG TCTTCGTATT GAAACCATAG ACCTTCTCGA     1320

TTGTGTATTC AATGATGAAG GTGTTAATGA TTTTATCACT TAAAAAAAAA AAAAAA         1377
```

(2) INFORMATION FOR SEQ ID NO:21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
CAYGARGTSG TNGGNRAGGT NGTNGAGG                                  28
```

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
GGYTTNCCRT CNGTGTASAC RTCRTTG                                   27
```

(2) INFORMATION FOR SEQ ID NO:23:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
GGTGGTGGGG GAGGTGGTGG AGGTCGGGCC CGAGGTGGCC AAGTACGGCT TCGGCGACGT    60
GGTAGGCGTC GGGGTGATCG TTGGGTCGTG CCGCGAGTGC AGCCCCTGCA AGGCCAACGT   120
TGAGCAGTAC TGCAACAAGA AGATCTGGTC ATACAACGAC GTCTACACCG ACGGCAAACC   180
```